US006186947B1

(12) United States Patent
Ouchi

(10) Patent No.: US 6,186,947 B1
(45) Date of Patent: Feb. 13, 2001

(54) SECTOR SCANNING, INTRACAVITARY ULTRASONIC PROBE

(75) Inventor: Teruo Ouchi, Saitama (JP)

(73) Assignee: Asahi Kogaku Kogyo Kabushiki Kaisha, Tokyo (JP)

( * ) Notice: Under 35 U.S.C. 154(b), the term of this patent shall be extended for 0 days.

(21) Appl. No.: 09/361,559

(22) Filed: Jul. 27, 1999

(30) Foreign Application Priority Data

Jul. 29, 1998 (JP) .................................................. 10-213825

(51) Int. Cl.⁷ ........................................................ A61B 8/00
(52) U.S. Cl. ............................ 600/439; 600/462; 600/459
(58) Field of Search .................................. 600/437, 439, 600/462, 459, 443, 464

(56) References Cited

U.S. PATENT DOCUMENTS 5,050,588 * 9/1991 Grey et al. ............................ 600/439
5,123,404 * 6/1992 Takayama ............................. 600/439
5,687,729 * 11/1997 Schaetzle ............................. 600/439
5,733,244 3/1998 Yasui et al. .

FOREIGN PATENT DOCUMENTS 3-2536 1/1991 (JP) .

* cited by examiner

Primary Examiner—Marvin M. Lateef
Assistant Examiner—Maulin Patel
(74) Attorney, Agent, or Firm—Greenblum & Bernstein, P.L.C.

(57) ABSTRACT

A sector scanning, intracavitary ultrasonic probe has an ultrasonic oscillator array (20) provided at the tip (12) of a cavity insertion portion (11) for scanning a sectorial area lateral to the tip (12). Individual ultrasonic oscillators (21) of the array (20) are inclined to be perpendicular to respective radial lines converging to a point located opposite from the sectorial area with respect to the ultrasonic oscillators, and are aligned straight in equidistant positions from the longitudinal axis of the tip (12) of the insertion portion (11).

13 Claims, 5 Drawing Sheets

SECTOR SCANNING, INTRACAVITARY ULTRASONIC PROBE

BACKGROUND OF THE INVENTION

The present invention relates to a sector scanning, intracavitary ultrasonic probe that is inserted into a body cavity for obtaining an ultrasonic cross-sectional image.

An intracavitary ultrasonic probe of an initial stage is designed such that ultrasonic oscillators are arranged on a line, and each of the ultrasonic oscillators transmits and receives ultrasonic waves in a direction perpendicular to that line.

A drawback encountered with this ultrasonic probe is that a range of ultrasonic wave scanning to obtain a sectional image is structurally restricted by the length of the ultrasonic oscillators arranged. Therefore, the increase of the ultrasonic wave scanning range to obtain a wider sectional image inevitably requires the ultrasonic oscillators to be arranged over the increased length, which makes it difficult to insert the probe into the body cavity.

To overcome this drawback associated with this ultrasonic probe, a sector scanning, intracavitary ultrasonic probe has been developed. The sector scanning, intracavitary ultrasonic probe has ultrasonic oscillators arrayed on an arcuate line so as to scan an area outside of and lateral to the tip of the insertion portion of the probe in a sector manner. Thus, the scanning range can be increased without the increase of the arrangement length of the ultrasonic oscillators.

In the sector scanning, intracavitary ultrasonic probe, the individual ultrasonic oscillators arrayed on the arcuate line and accommodated in the insertion portion of the probe, the insertion portion of the probe partially bulges out to present an arcuate, convex shape. Because of this shape, the probe is commonly called "a convex type".

A problem with the ultrasonic probe of the convex type is that the partial bulge of the tip of the insertion portion increases its outside dimensions, thereby increasing the pain the patient may feel while the probe is inserted for inspection purposes.

Another problem is that the probe cannot be used with a small-diameter endoscope since its treatment tool insertion channel is too small in diameter to permit the passage of the bulging part of the probe.

SUMMARY OF THE INVENTION

The present invention has been accomplished under these circumstances and has as an object providing a sector scanning, intracavitary ultrasonic probe that can be formed in sufficiently small outside dimensions so that the pain that may be caused to the patient can be reduced as well as the probe can be used with a small-diameter endoscope as it is passed through the treatment tool insertion channel.

The stated object of the invention can be attained by a sector scanning, intracavitary ultrasonic probe having an array of ultrasonic oscillators provided at the tip of a cavity insertion portion for scanning a sectorial area lateral to said tip, characterized in that the individual ultrasonic oscillators of the array are inclined to be perpendicular to respective radial lines converging to a point located opposite from the sectional area with respect to the ultrasonic oscillators, and the individual ultrasonic oscillators are aligned straight in equidistant positions from the longitudinal axis of the tip of said insertion portion.

If desired, an inflatable balloon that encloses said array of ultrasonic oscillators may be detachably provided at the tip of said insertion portion.

Objective optics in an optical examining system may be provided at the tip of said insertion portion. In this case, said array of ultrasonic oscillators may perform ultrasonic scan in directions substantially parallel to the direction of examination by said optical examining system.

The present disclosure relates to the subject matter contained in Japanese patent application No. Hei. 10-213825 (filed on Jul. 29, 1998), which is expressly incorporated herein by reference in its entirety.

DESCRIPTION OF THE PREFERRED EMBODIMENT

Several embodiments of the invention are described below with reference to the accompanying drawings.

Figure 1:
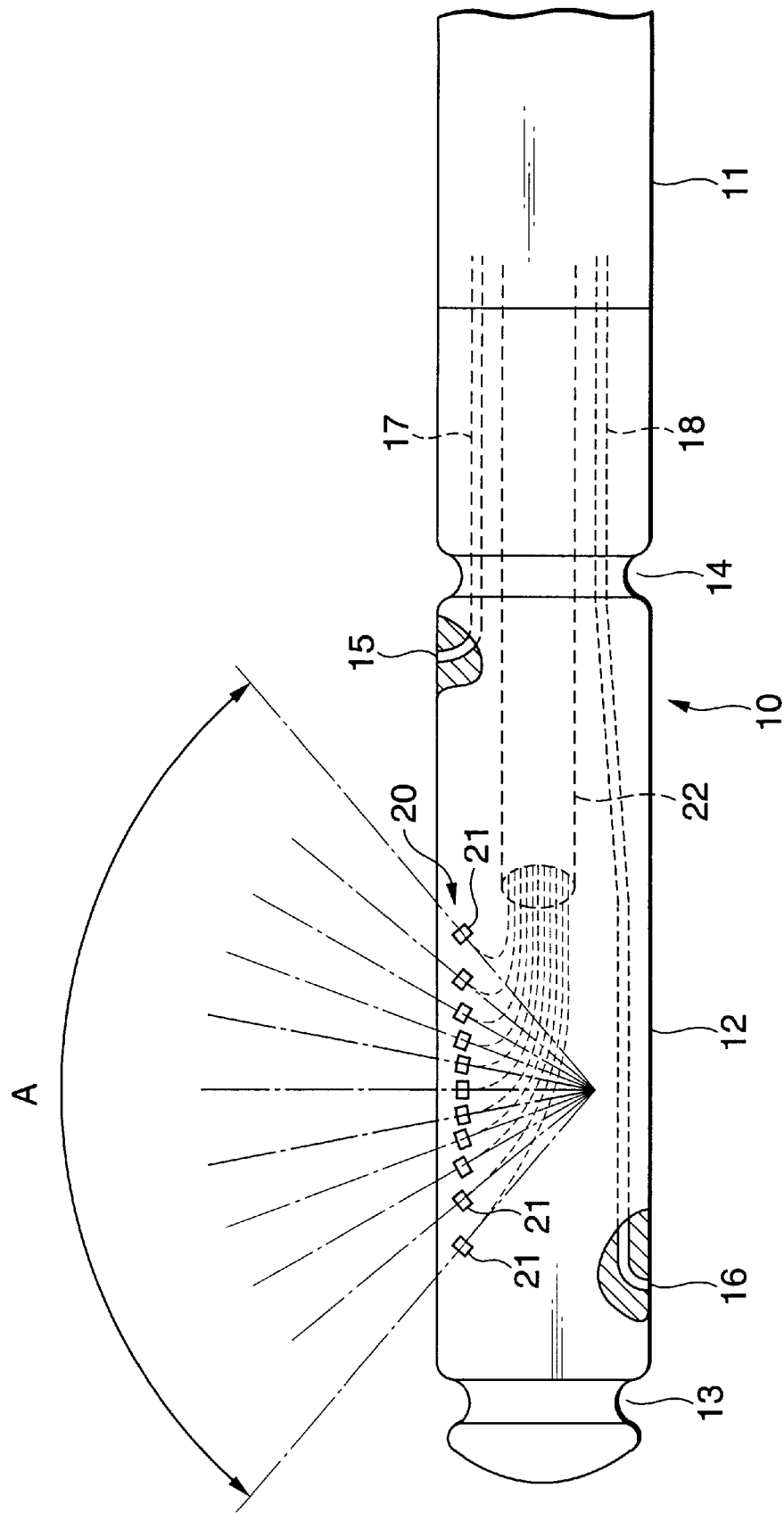
FIG. 1 is a side view of a sector scanning, intracavitary ultrasonic probe according to a first embodiment of the invention.

FIG. 1 shows the tip portion of an ultrasonic probe 10 according to a first embodiment of the invention. The probe 10 is inserted into a body cavity either directly or otherwise it is passed through the treatment tool insertion channel of an endoscope (not shown) to be inserted into the body cavity.

The probe 10 is made up of a flexible tube 11 and a cylindrical tip forming member 12 that is coupled straight to the tip of the flexible tube 11. A pair of circumferential grooves 13 and 14 are formed near the front and rear ends of the tip forming member 12 so that an inflatable balloon may be fitted as required.

A balloon is fitted in such a way that it completely encloses an ultrasonic oscillator array 20; it is inflated or deflated as degassing water is fed in through an intake 15 or discharged through a drain 16. The intake 15 and the drain 16 are open to the surface of the tip forming member 12 between the two circumferential grooves 13 and 14. Indicated by 17 and 18 are a water feed pipe and a water discharge pipe, respectively, that extend through the flexible tube 11 to be connected to the intake 15 and the drain 16, respectively.

The ultrasonic oscillator array 20 is made up of a number of ultrasonic oscillators 21 arranged in a line. The individual ultrasonic oscillators 21 are inclined to be perpendicular to respective radial lines converging to a point located opposite from a scan range A with respect to the ultrasonic oscillators 21. The ultrasonic oscillators 21 are provided near the surface of the tip forming member 12 while they are aligned straight in a line parallel to the longitudinal axis of the tip forming member 12.

Being arranged that way, the individual ultrasonic oscillators 21 successively transmit and receive signals of ultrasonic waves to scan a sectorial area (the scan range A) which is lateral to the tip forming member 12. This is what is commonly called "sector scan". Indicated by 22 is a signal cable that is made up of a bundle of signal lines connected to the individual ultrasonic oscillators 21 and which is passed through the flexible tube 11.

For the sake of convenience, the array is shown to consist of 11 ultrasonic oscillators 21. In practical applications, about 32 to 64 ultrasonic oscillators 21 need be arranged to scan a range of about 50 to 100 degrees.

As mentioned above, the individual ultrasonic oscillators 21 in the array 20 are situated near the surface of the tip forming member 12 between the two circumferential grooves 13 and 14 such that they are aligned on a straight line that is parallel to the longitudinal axis of the tip forming member 12. These ultrasonic oscillators 21 are in equidistant positions from the longitudinal axis of the tip forming member 12.

Although the probe 10 is of a sector scanning type that performs ultrasonic scan through a sectorial area lateral to the tip forming member 12, the above-described design obviates the need to form the tip forming member 12 in a thick convex shape, thereby reducing the pain that may be caused to the patient while the probe is inserted into a body cavity. As a further advantage, the probe can be passed through the treatment tool insertion channel of a small-diameter endoscope and this contributes to widen the range of examinations to which the probe can be applied.

Figure 2:
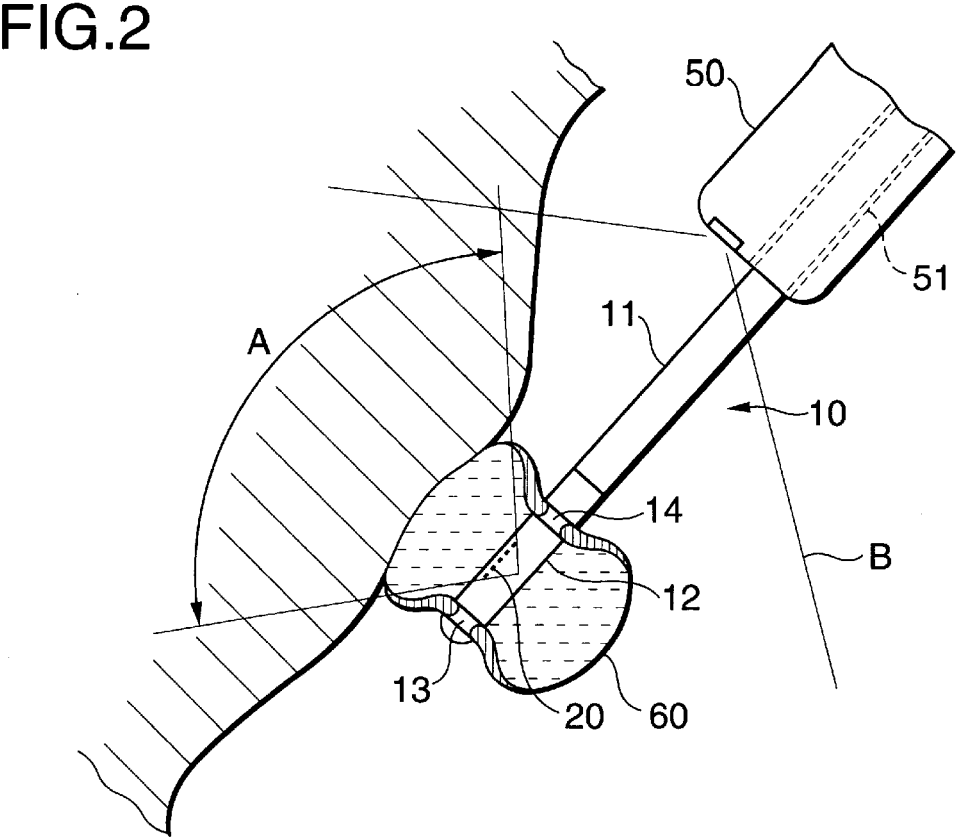
FIG. 2 is a sketch showing how the sector scanning, intracavitary ultrasonic probe according to the first embodiment of the invention is used.
Figure 3:
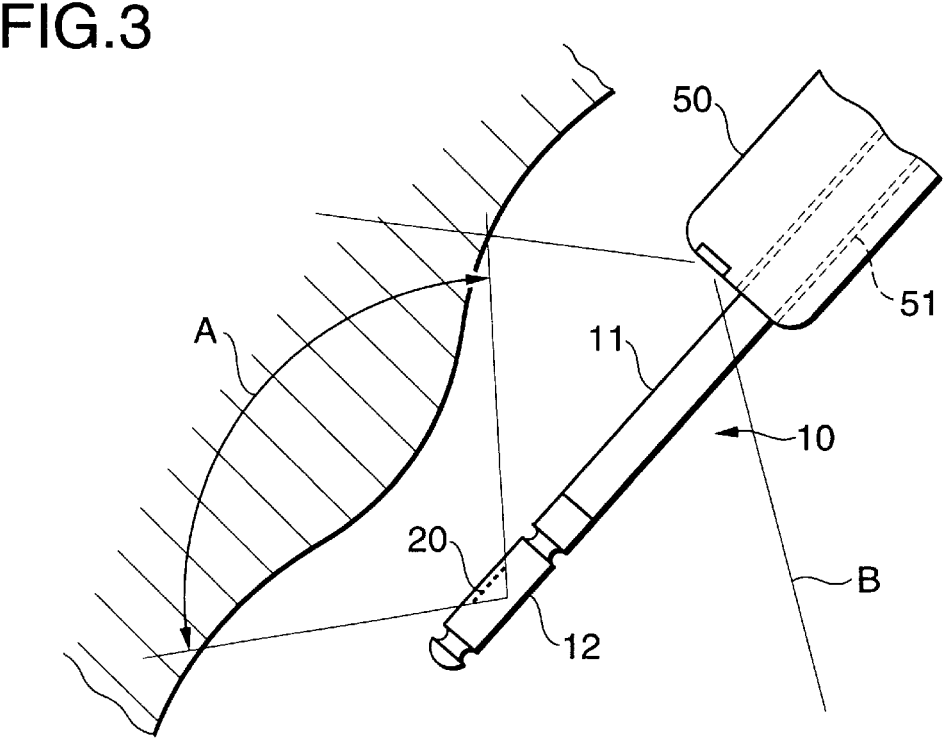
FIG. 3 is a sketch showing another way in which the sector scanning, intracavitary ultrasonic probe according to the first embodiment of the invention is used.

FIGS. 2 and 3 show how the ultrasonic probe 10 according to the embodiment described above is inserted into a body cavity through a treatment tool insertion channel 51 of an endoscope 50. The illustrated endoscope 50 is of a forward viewing type that produces a forward oriented viewing range B. However, this is not the sole case of the invention and the probe 10 may be used with a lateral viewing type or an angle viewing type.

If a target body cavity into which the ultrasonic probe 10 cannot be filled with water or other fluid, a balloon 60 is fitted to the tip forming member 12 and brought into intimate contact with the surface of mucosa as shown in FIG. 2. If the target body cavity can be filled with water or other fluid, the ultrasonic probe 10 may be used without balloon as shown in FIG. 3.

Figure 4:
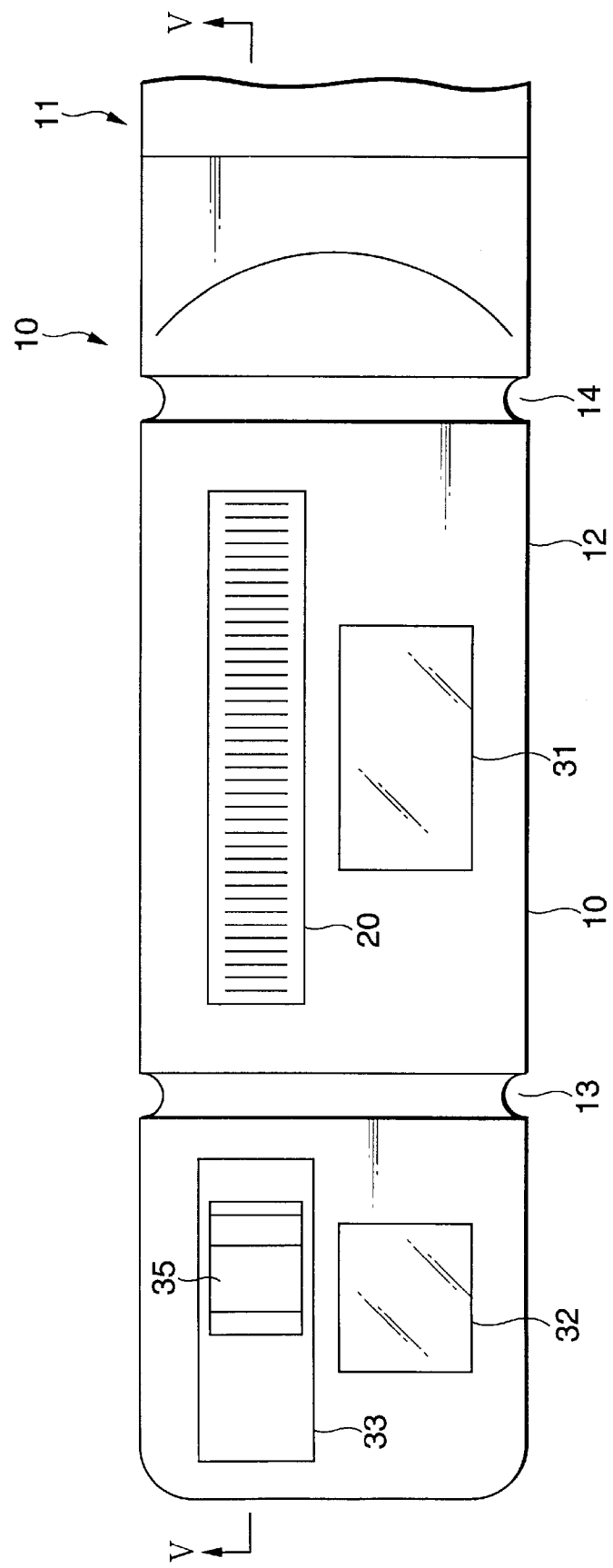
FIG. 4 is a plan view of a sector scanning, intracavitary ultrasonic probe according to a second embodiment of the invention.
Figure 5:
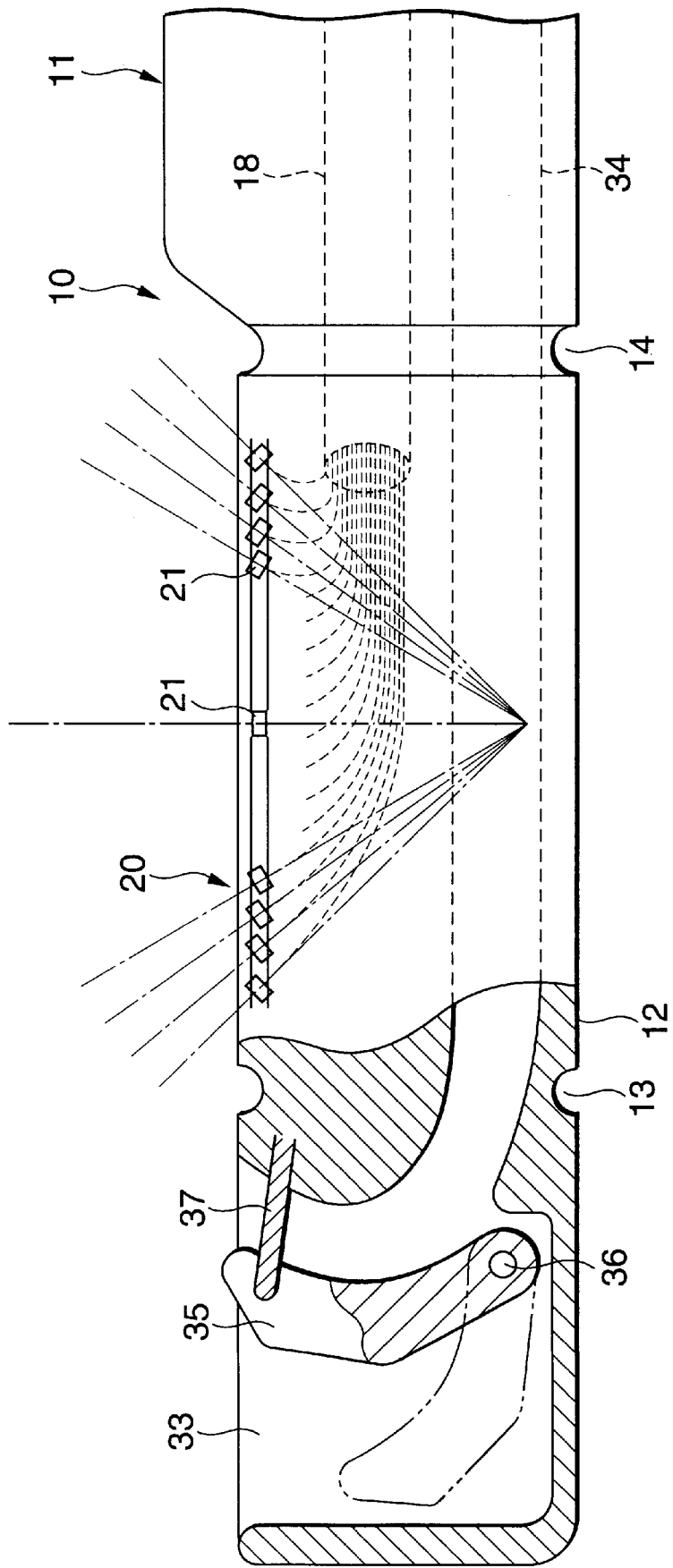
FIG. 5 is a section V—V of FIG. 4.

FIGS. 4 and 5 show an ultrasonic probe 10 according to a second embodiment of the invention, in which the ultrasonic oscillator array 20 is built into a lateral viewing endoscope to make a so-called "ultrasonic endoscope". FIG. 4 is a plan view of the ultrasonic endoscope and FIG. 5 is a section V—V of FIG. 4.

An optical viewing window 31 and the ultrasonic oscillator array 20 are provided side by side. Since the direction in which the ultrasonic oscillator array 20 performs ultrasonic scan is substantially parallel to the direction of viewing through the window 31, the operator can examine an object lying in the same direction as the scan range A of the ultrasonic oscillator array 20. Shown by 32 is an illumination window through which illuminating light is issued toward the viewing range.

Objective optics, a solid-state imaging device (or an imageguide fiber bundle) and so forth are provided at sites behind the viewing window 31. A lightguide fiber bundle and so forth are provided at a site behind the illumination window 32. These components are known in the art and need not be shown in FIGS. 4 and 5.

A slot 33 is formed in the tip forming member 12 and juxtaposed with respect to the illumination window 32. A treatment tool erecting plate 35 is provided in the slot 33 for changing the direction in which the tip portion of a treatment tool passed through the treatment tool insertion channel 34 projects.

As shown in FIG. 5, the treatment tool erecting plate 35 is provided in the slot 33 such that it is pivotal about a shaft 36. Although not shown, a handling section closer to the operator is manipulated to move a maneuvering wire 37 back and forth, whereupon the treatment tool erecting plate 35 pivots to have the tip of the treatment tool project in a desired direction.

Figure 6:
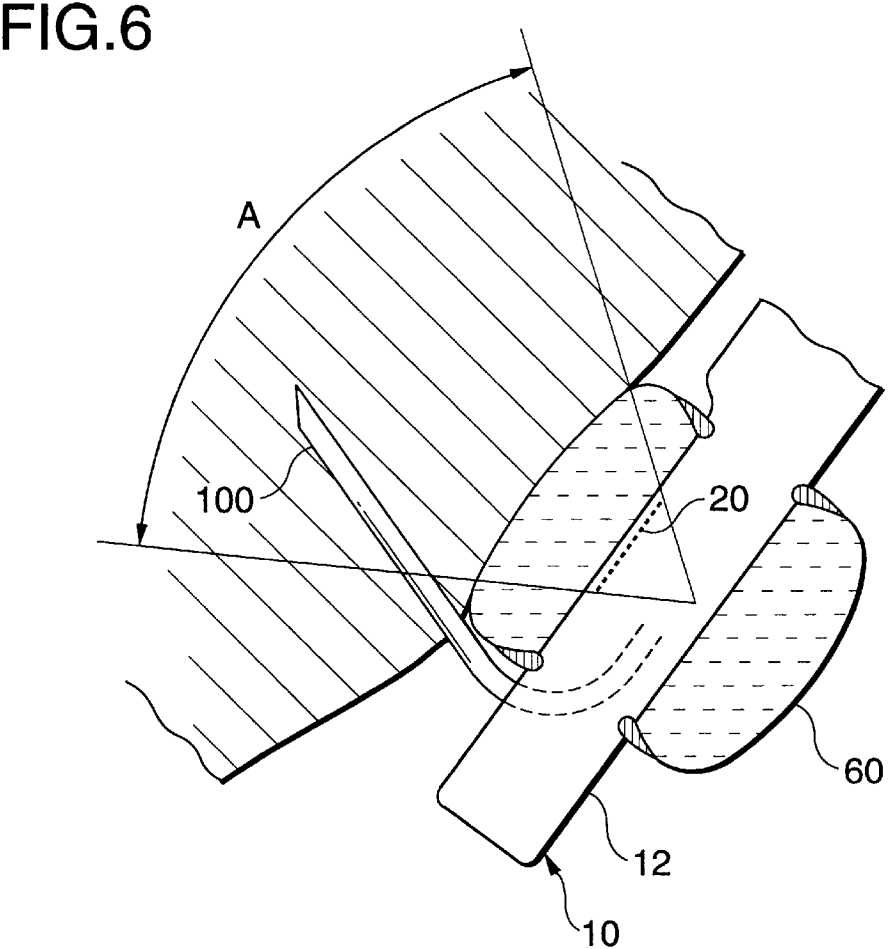
FIG. 6 is a sketch showing how the sector scanning, intracavitary ultrasonic probe according to the second embodiment of the invention is used.

FIG. 6 shows how the ultrasonic probe 10 according to the second embodiment of the invention is used within a body cavity. As the operator examines optically the mucosa on the surface of a diseased part via the viewing window 31, the ultrasonic oscillator array 20 transmits ultrasonic waves into the diseased part and receives the reflected waves, thereby obtaining an ultrasonic cross-sectional image of an area under the mucosa. The operator may then use a treatment tool 100 such as an injection device to perform the necessary treatment on the diseased part.

Figure 7:
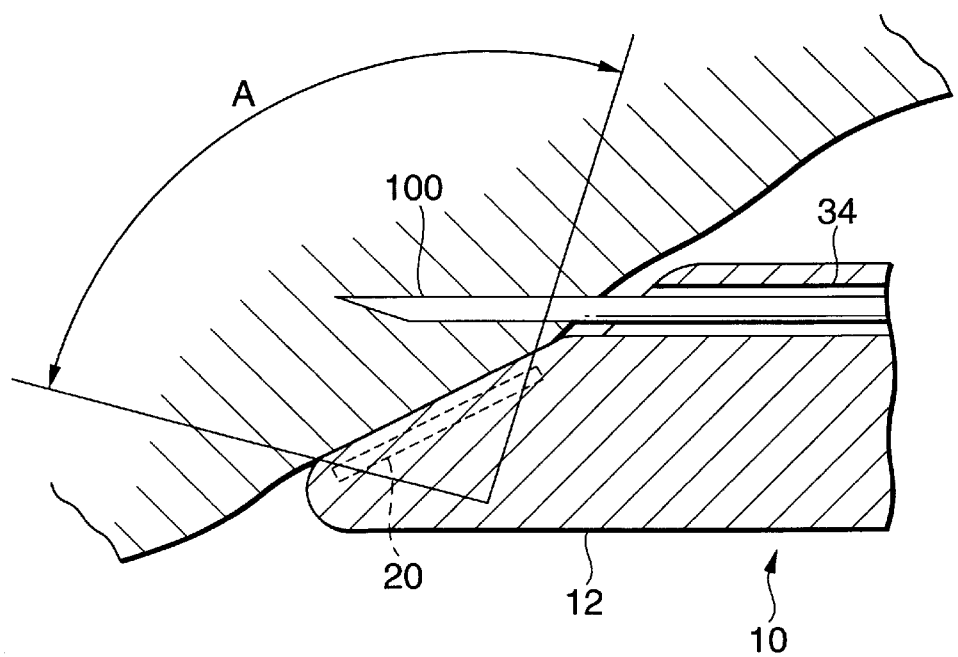
FIG. 7 is a longitudinal section of a sector scanning, intracavitary ultrasonic probe according to a third embodiment of the invention.

It should be noted that the invention is by no means limited to the two embodiments described above. For example, as shown in FIG. 7, the ultrasonic oscillator array 20 of the invention may be built into an angle viewing endoscope so that a sectorial area is scanned with ultrasonic waves within an optical viewing range created at an angle in forward direction. As can be seen in FIG. 7, since the distal end of the tip forming member 12 of the angle viewing endoscope can be formed into a tapered shape, the resistance caused between the distal end portion and the living tissue in the body cavity can be made smaller in comparison with the case of the convex-shaped distal end, which contributes to the reduction of pain on a patient.

In the sector scanning, intracavitary ultrasonic probe of the invention that performs an ultrasonic scan of a sectorial area lateral to the tip of the insertion of the probe, ultrasonic oscillators in an array are inclined to be perpendicular to radial lines converging to a point located opposite from the sectorial area and are arranged in equidistant positions from the longitudinal axis of the tip of the insertion portion. This contributes to the reduction of the outside dimensions of the probe to sufficiently small values that can reduce the pain that may be caused to the patient as well as the probe can be used with a small-diameter endoscope as it is passed through the treatment tool insertion channel.

What is claimed is:

1. A sector scanning, intracavitary ultrasonic probe having an array of ultrasonic oscillators provided at a tip of a cavity insertion portion for scanning a sectorial area lateral to said tip, wherein the individual ultrasonic oscillators of the array are inclined to be perpendicular to respective radial lines converging to a point located opposite from the sectorial area with respect to the ultrasonic oscillators, and the ultrasonic oscillators are aligned straight in equidistant positions from a longitudinal axis of the tip of said insertion portion.

2. The sector scanning, intracavitary ultrasonic probe according to claim 1, wherein an inflatable balloon that encloses said array of ultrasonic oscillators is detachably provided at the tip of said insertion portion.

3. The sector scanning, intracavitary ultrasonic probe according to claim 1, wherein objective optics in an optical examining system is provided at the tip of said insertion portion.

4. The sector scanning, intracavitary ultrasonic probe according to claim 3, wherein said array of ultrasonic oscillators performs ultrasonic scan in directions substantially parallel to the direction of examination by said optical examining system.

5. An ultrasonic scanning system to be inserted into a body cavity for scanning a diseased part of a patient along a sectorial area, said system comprising:

an insertion portion to be inserted into the body cavity, the insertion portion having a tip forming member; and, a number of ultrasonic oscillators embedded in the tip forming member, the oscillators being arrayed on a straight line, and inclined to be perpendicular to respective radial lines converging to a point located opposite from the sectorial area with respect to the oscillators.

6. The ultrasonic scanning system according to claim 5, wherein the tip forming member is cylindrical.

7. The ultrasonic scanning system according to claim 6, wherein each of the oscillators is spaced from a longitudinal axis of the tip forming member at the same distance.

8. The ultrasonic scanning system according to claim 5, wherein a part of the tip forming member is linearly tapered.

9. The ultrasonic scanning system according to claim 8, wherein each of the oscillators is spaced from a surface of said part at the same distance.

10. The ultrasonic scanning system according to claim 5, further comprising:

a pair of annular grooves formed on the tip forming member, wherein the ultrasonic oscillators are disposed between the annular grooves.

11. The ultrasonic scanning system according to claim 7, further comprising:

an optical examining system having objective optics, the objective optics being arranged at the tip forming member.

12. The ultrasonic scanning system according to claim 11, wherein the ultrasonic oscillators provide a scanning to an object to be located radially with respect to the longitudinal axis, and the optical examining system optically obtains an image of the object to be located radially with respect to the longitudinal axis.

13. The ultrasonic scanning system according to claim 9, wherein objective optics in an optical examining system is provided at the tip forming member, and the sectorial area is within an optical viewing range created by the objective optics.

* * * * *